United States Patent [19]

Sandnes et al.

[11] Patent Number: 5,589,595
[45] Date of Patent: Dec. 31, 1996

[54] PROCESS FOR TETRAAZACYCLOALKANE PREPARATION

[75] Inventors: Rolf W. Sandnes; Kjell Undheim; Michel Gacek, all of Oslo, Norway; Janis Vasilevskis, Wayne, Pa.

[73] Assignee: Nycomed Imaging AS, Oslo, Norway

[21] Appl. No.: 483,189

[22] Filed: Jun. 7, 1995

[30] Foreign Application Priority Data

Mar. 10, 1995 [GB] United Kingdom .................. 9504922

[51] Int. Cl.$^6$ .......................... C07D 257/02; A61K 49/00
[52] U.S. Cl. .......................... 540/474; 544/345; 544/346; 548/302.1; 534/15; 424/9.323
[58] Field of Search .................................. 540/474, 451, 540/460; 548/302.1; 544/345, 346; 424/9.323; 534/15

[56] References Cited

U.S. PATENT DOCUMENTS

| | | | |
|---|---|---|---|
| 3,485,818 | 12/1969 | Thompson | 260/239 |
| 4,085,106 | 4/1978 | Atkins | 260/256.4 |
| 5,047,527 | 9/1991 | Handel et al. | 540/474 |
| 5,284,944 | 2/1994 | Madison et al. | 540/474 |
| 5,386,028 | 1/1995 | Tilsam et al. | 540/474 |
| 5,424,423 | 6/1995 | Uggerl et al. | 540/474 |
| 5,434,262 | 7/1995 | Guilard et al. | 540/474 |

FOREIGN PATENT DOCUMENTS

| | | |
|---|---|---|
| 0232751A1 | 8/1987 | European Pat. Off. . |
| 0292689A2 | 11/1988 | European Pat. Off. . |
| 0427595A1 | 5/1991 | European Pat. Off. . |

OTHER PUBLICATIONS

Anelli et al. J. Chem. Soc., Perkin Trans 1, 1995 pp. 2995–3003.
R. A. Kolinski et al., "Ring Inversion in Polycyclic Tetraamines", Tetrahedron Letters, vol. 22, No. 23, pp. 2217–2220, 1981.
Geoffrey Lawrance et al., "Macrocyclic Tetraamines from Reaction of the (1,10–Diamino-4,7–Diazadecane) Cation . . . ", Polyhedron, vol. 6, No. 6, pp. 1291–1294, 1987.
Andres De Blas et al., "Amides and Sulfonamides: Efficient Molecular Padlocks for the Template Synthesis of Azacyclam (1,3,5,8,12–Pentaazacyclotetradecane) Macrocycles", J. Chem. So. Dalton Trans. 1993, pp. 1411–1416.
E. K. Barefield, et al., "(1,4,811–Tetraazacyclotetradecane) Nickel (II) Perchlorate and 1,4,8,11–Tetraazacyclotetradecane", Inorganic Syntheses, 1976, v. 16, pp. 220–225.
E. Kent Barefield, et al., "Synthesis of Macrocyclic Tetramines by Metal Ion Assisted Cyclization Reactions", Inorganic Chemistry, vol. 15, No. 6, 1976, p. 1370–1377.
Peter Comba et al., "Synthesis of a Thirteen–membered Tetra–azamacrocycle employing Formaldehyde and Nitroalkanes . . . ", J. Chem. Soc. Dalton Trans. 1988, pp. 497–502.
Jaroslaw Jazwinski et al., "Tricyclic Tetraamines by Glyoxal—Linear Tetraamine Condensation", Tetrahedron Letters, vol. 22, No. 18, pp. 1711–1714, 1981.
E. Kent Barefield, "A New Synthesis of 1,4,8,11–Tetraazacyclotetradecane (Cyclam) via the Nickel (II) Complex", Inorganic Chemistry, vol. 11, No. 9, 1972, pp. 2273–2274.
Gary R. Weisman et al., "Tetracyclic Tetramines by Glyoxal–Macrocyclic Tetraamine Condensation", Tetrahedron Letters, vol. 21, pp. 335–338. 1980.

*Primary Examiner*—Mukund J. Shah
*Assistant Examiner*—Pavanaram K. Sripada
*Attorney, Agent, or Firm*—Fish & Richardson PC

[57] ABSTRACT

The present invention provides a synthetic route for tetraazacycloalkane preparation which facilitates heteropoly-N-alkylation of the macrocyclic product, and is thereby beneficial for the production of chelating agents and chelates useful in diagnostic imaging. The process involves (i) reacting a tetraazaalkane with a bridging agent to couple four amine nitrogens of said tetraazaalkane to a bridging moiety to yield a fused tricyclic intermediate, (ii) reacting said intermediate to introduce an alkylene bridge between the secondary amine nitrogens in the outer rings of the fused tricyclic intermediate, optionally by decoupling an alkanediylidene bridging moiety from the tertiary amine nitrogens at the ring fusion sites of the fused tricyclic intermediate, and (iii) where necessary, decoupling said bridging moiety to yield a macrocyclic tetraazacycloalkane.

27 Claims, No Drawings

PROCESS FOR TETRAAZACYCLOALKANE PREPARATION

FIELD OF THE INVENTION

This invention relates to a novel process for the preparation of tetraazacycloalkanes, in particular cyclen and ring-substituted cyclen derivatives.

BACKGROUND OF THE INVENTION

In the field of magnetic resonance imaging, various lanthanide chelates of cyclen-derivative macrocyclic chelating agents have been proposed. Two, GdHP-DO3A (ProHance from Squibb) and GdDOTA (Dotarem from Guerbet), are available commercially. These macrocyclic chelating agents form particularly stable chelate complexes with the contrast-generating paramagnetic metal ions and thus are suitable carriers for the metal ions to ensure appropriate biodistribution and elimination.

Cyclen itself (1,4,7,10-tetraazacyclododecane) is a key and somewhat expensive intermediate in the preparation of these macrocyclic chelants.

Production of cyclen's tetraaza macrocycle can be by a variety of synthetic routes, for example via diamine:diamine or triamine:monoamine cyclic condensations such as are described by Tweedle in EP-A-232751 and EP-A-292689. Such condensations generally produce N-substituted cyclen derivatives in which the ring nitrogens are protected by tosyl or mesyl groups which then have to be removed before the cyclen can be alkylated to yield the macrocyclic chelating agent. Detosylation involves high temperature treatment with sulphuric acid, a commercially unattractive route. Detosylation moreover requires continuous extraction with chloroform over a period of days making it an environmentally unattractive procedure. Mesylation and demesylation are similarly difficult and unattractive on a commercial scale.

We have now found that macrocyclic tetraazacycloalkanes, such as cyclen, can advantageously be prepared from acyclic tetraazaalkanes by a cyclization process which involves first coupling the four nitrogens of the starting material to a bridging agent to produce a tricyclic intermediate and then converting this intermediate to the tetraaza-macrocycle.

In effect, the bridging moiety in the tricyclic intermediate, which can be a monoatomic or polyatomic entity, serves as a template to present the terminal nitrogens of the initially acyclic tetramine in a suitable configuration for the ring closing cyclization. Indeed, in one embodiment, the bridging moiety can itself provide the molecular subunit which forms the bridge between the terminal nitrogens to form the tetraaza-macrocycle.

SUMMARY OF THE INVENTION

Viewed from one aspect, the invention thus provides a process for the preparation of macrocyclic tetraazacycloalkanes, said process comprising (i) reacting a tetraazaalkane with a bridging agent to couple four amine nitrogens of said tetraazaalkane to a bridging moiety to yield a fused tricyclic intermediate, (ii) reacting said intermediate to introduce an alkylene bridge between the secondary amine nitrogens in the outer rings of the fused tricyclic intermediate, optionally by decoupling an alkanediylidene bridging moiety from the tertiary amine nitrogens at the ring fusion sites of the fused tricyclic intermediate, and (iii) where necessary, decoupling said bridging moiety to yield a macrocyclic tetraazacycloalkane.

The process of the invention is especially suited to the production of cyclen and substituted cyclens and the discussion hereafter will be in relation to the production of 1,4,7,10-tetraazacyclododecanes. Other tetraazacycloalkanes, in particular those with 13 to 16 ring members, may be produced analogously and the scope of the invention extends to include such analogous processes.

DETAILED DESCRIPTION OF THE INVENTION

The macrocylic tetraazacyclododecanes produced by the process of the invention will conveniently be of formula I

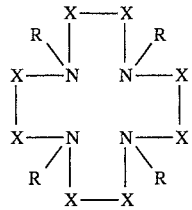

where R is hydrogen or optionally substituted alkyl and X is $CH_2$, CHR or a carbonyl group.

The tricyclic intermediates formed during the process of the invention preferably have a 5,5,5 or 5,6,5 tricyclic structure (the numbers referring to the numbers of ring atoms in each of the fused rings), e.g.

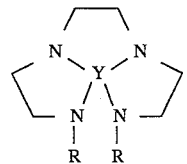
(5,5,5)

or

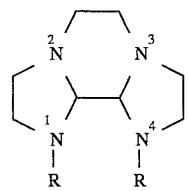
(5,6,5)

where Y is a carbon atom or a metal ion. The backbone carbons of these intermediates may if desired be substituted, for example by R groups.

Examples of non-hydrogen R groups include $C_{1-6}$ alkyl groups optionally substituted by hydroxy, $C_{1-6}$ alkoxy, aryl (e.g. phenyl), carboxy or phosphonic acid groups or esters or amides thereof.

The formation of the tricyclic intermediate is a particularly important aspect of the process of the invention as it positions the terminal nitrogens for reaction with a bridging moiety to produce the tetraazamacrocycle or alternatively allows direct conversion to the tetraazamacrocycle by the decoupling of the $C_2$ bridge of the 5,6,5 intermediate from the mid-chain nitrogens.

The initial step in the process of the invention particularly preferably involves a reaction with glyoxal to produce the 5,6,5 tricyclic intermediate, i.e.

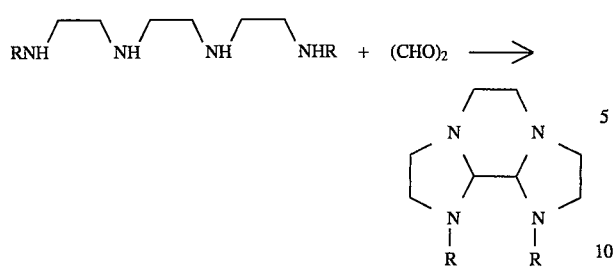

The backbone carbons on the tetraamine starting compound may if desired be substituted by non-hydrogen R groups as may be the terminal nitrogens.

The conversion from the 5,6,5 tricyclic intermediate to the tetraazamacrocycle may be accomplished in a variety of ways:

(A) reaction with a difunctional bridging agent serving to introduce a $C_2$ bridge, for example a haloacetylhalide, an allyl halide epoxide, or a compound of formula:

(where Lv is a displaceable leaving group such as a halogen atom (e.g. chlorine or bromine) or a sulphonyloxy group such as OMs or OTs). This reaction is then followed by decoupling of the $C_2$ bridging moiety, for example by reaction with hydroxylamine or an acid such as HBr. Illustrative of this reaction procedure is the following sequence:

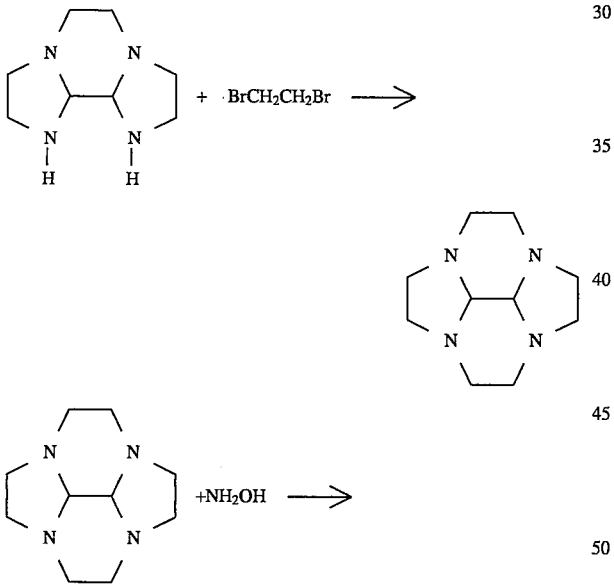

(B) reaction with glyoxal with subsequent reduction, e.g. by catalytic hydrogenation over palladium, and decoupling of the $C_2$ bridging moiety. The decoupling can be effected as described under (A) above. Illustrative of this reaction sequence is the following procedure:

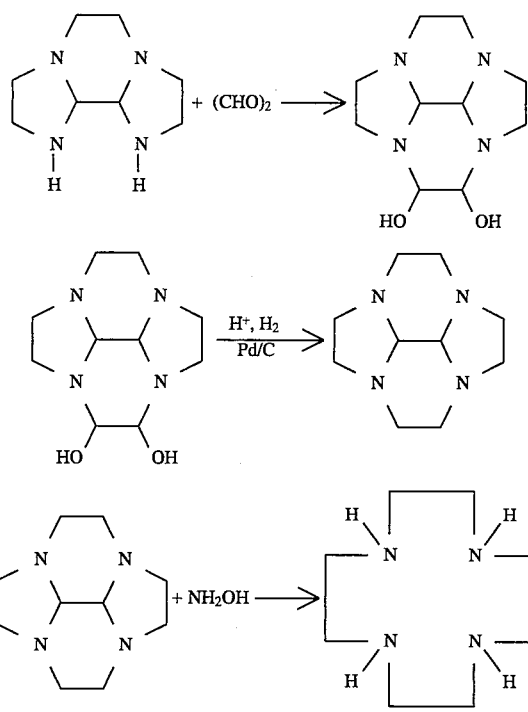

(C) tetramine reaction with glyoxal with subsequent conversion to the tetraazamacrocycle may be effected as a one-pot reaction, for example using the reaction sequence:

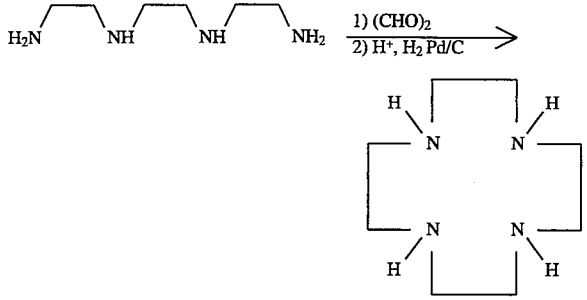

(D) reaction to partially decouple the central bridging moiety by metallation, for example with $Cu^{2+}$ or $Ni^{2+}$, followed by demetallation, e.g. by hydrogenation or cyanide treatment. In this way the $C_2$ bridging moiety can be transformed into a sub-unit of the final macrocycle. Illustrative of this reaction sequence are the following reactions:

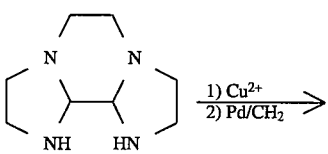

-continued

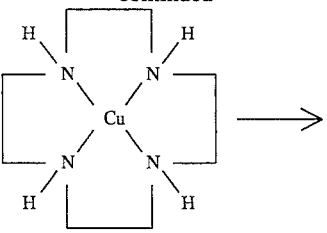

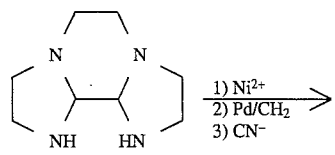

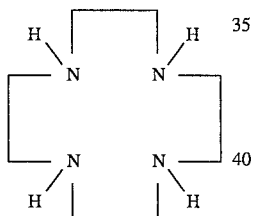

Besides the 5,6,5 tricyclic intermediate, other tricyclic intermediates can be involved in the process of the invention and in one particular embodiment a single carbon bridging moiety may be introduced to provide a 5,5,5 intermediate, i.e.

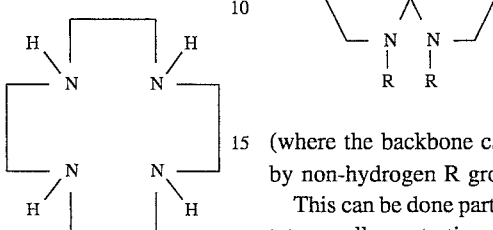

(where the backbone carbons can optionally be substituted by non-hydrogen R groups).

This can be done particularly effectively by reaction of the tetraazaalkane starting material with an alkylorthocarbonate, for example $C(OC_2H_5)_4$, in the following reaction:

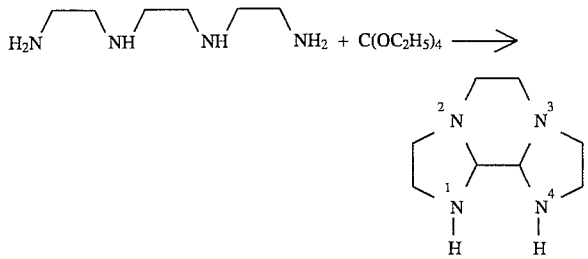

The tetraazacycloalkane can then be produced by coupling the 1 and 4 nitrogens and decoupling the $C_1$ bridge. The coupling of the 1 and 4 nitrogens can involve reaction with a bifunctional reagent, substantially as described under (A) above, or alternatively may involve cyclizing a functionally substituted group pendent from one of these nitrogens, for example an alkoxycarbonylmethyl group. Examples of appropriate reaction schemes are as follows:

(E) reaction of the 5,5,5 intermediate with a bifunctional bridging agent followed by decoupling of the $C_1$ bridge, for example using the following scheme:

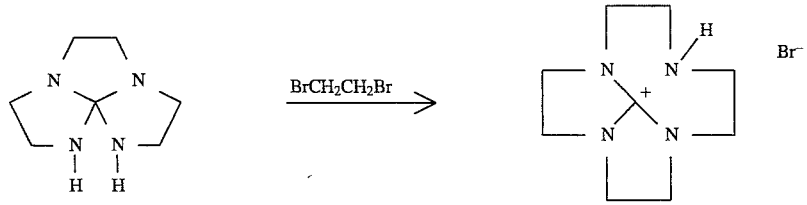

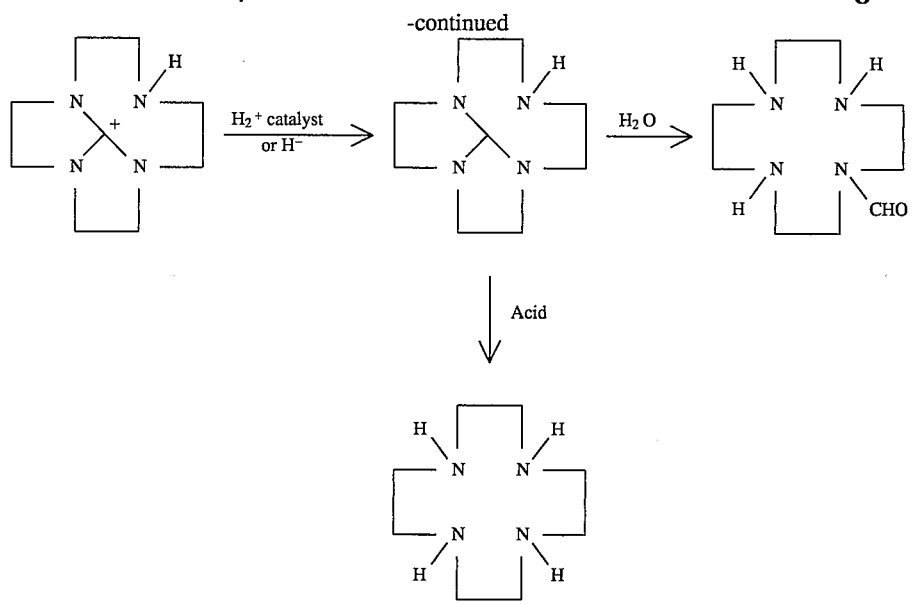

(F) cyclizing a functional group pendent from an outer ring nitrogen, e.g. as follows:

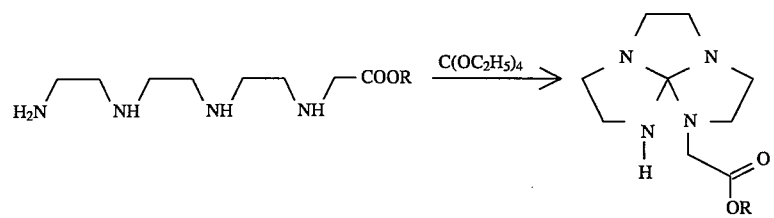

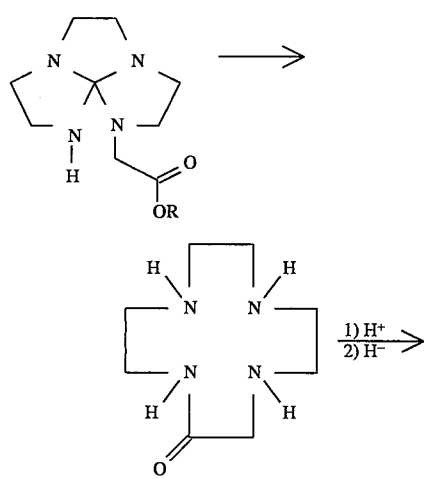

The pendent protected carboxymethyl group can be present in the initial acyclic tetraazaalkane reagent or can be introduced by alkylation of the tricyclic intermediate. Thus for example the following reaction scheme may be used:

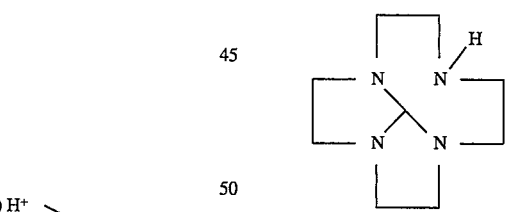

The 5,5,5 intermediate is particularly advantageous as it offers the possibility for monosubstitution of the ring-nitrogens during the macrocycle synthesis at the 5,5,8 intermediate stage. Thus reaction of 5,5,8

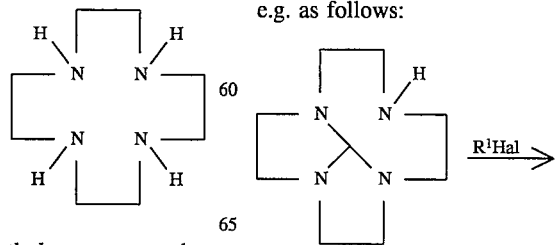

with water gives a mono-formyl product whereas reaction with an alkylating agent yields an N-monoalkylated 5,5,8 compound which can be converted by acid treatment, for example with sulphuric acid, to N-monoalkylated cyclen, e.g. as follows:

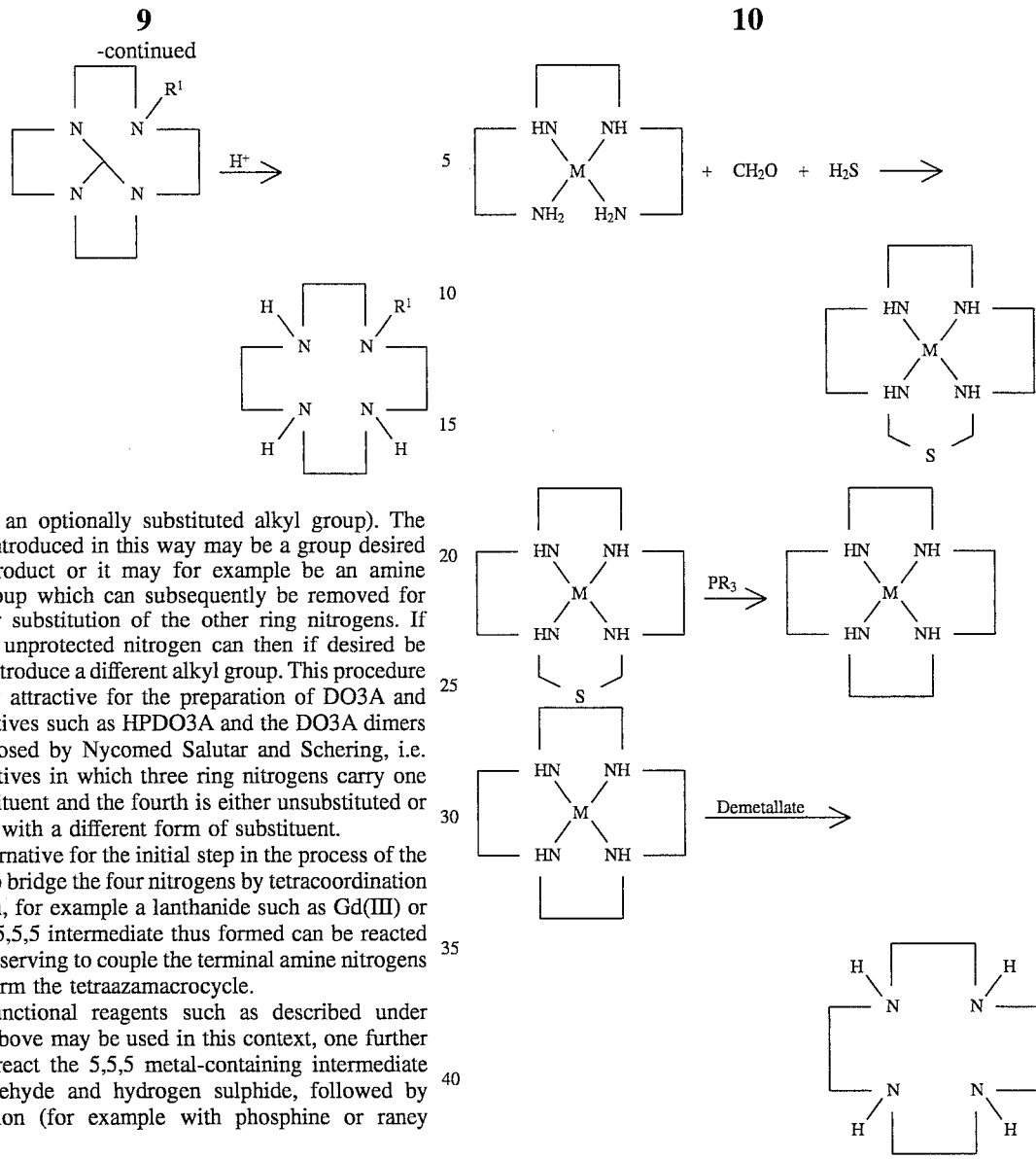

(where $R^1$ is an optionally substituted alkyl group). The alkyl group introduced in this way may be a group desired in the end product or it may for example be an amine protecting group which can subsequently be removed for example after substitution of the other ring nitrogens. If removed, the unprotected nitrogen can then if desired be alkylated to introduce a different alkyl group. This procedure is particularly attractive for the preparation of DO3A and DO3A derivatives such as HPDO3A and the DO3A dimers recently proposed by Nycomed Salutar and Schering, i.e. cyclen derivatives in which three ring nitrogens carry one form of substituent and the fourth is either unsubstituted or is substituted with a different form of substituent.

A third alternative for the initial step in the process of the invention is to bridge the four nitrogens by tetracoordination to a metal ion, for example a lanthanide such as Gd(III) or Dy(III). The 5,5,5 intermediate thus formed can be reacted with an agent serving to couple the terminal amine nitrogens together to form the tetraazamacrocycle.

While difunctional reagents such as described under scheme (A) above may be used in this context, one further option is to react the 5,5,5 metal-containing intermediate with formaldehyde and hydrogen sulphide, followed by desulphurisation (for example with phosphine or raney nickel).

These 5,5,5 metal intermediate conversions are illustrated by the following reaction schemes:

(G) reaction with a bifunctional bridging reagent followed by demetallation, for example as follows:

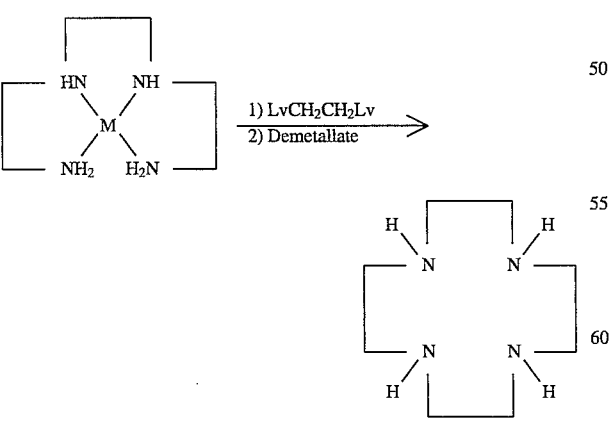

(H) reaction with formaldehyde and hydrogen sulphide followed by desulphurisation and demetallation, for example as follows:

In an alternative synthetic route, the $C_2$ centrally bridged cyclic tetraamine of route (A) above can be produced from a diamine starting material.

In this analogous reaction, because the starting material is a diamine rather an a tetraamine and the bridged intermediate is a 6,6, bicyclic compound rather than a 5,6,5 tricyclic compound, two N—N bridges have to be inserted rather than the one inserted in route (A).

This route (A') is as follows

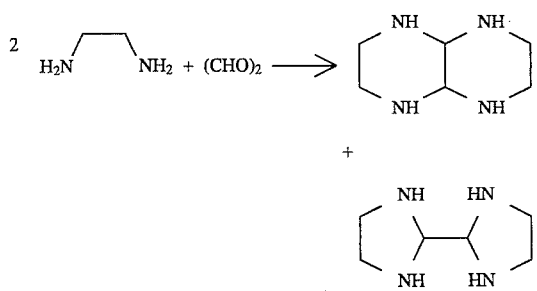

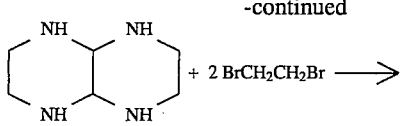

-continued

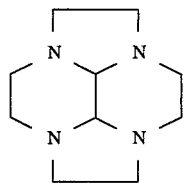

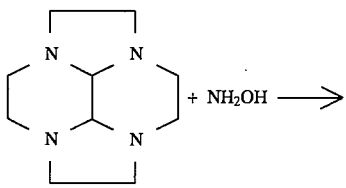

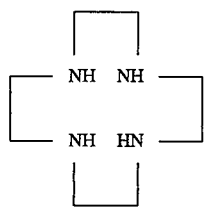

The diamine carbons may carry non-hydrogen R groups and the other difunctional bridging agents mentioned in connection with route (A) may be used in place of the dibromoethane.

This scheme represents a further aspect of the present invention. Thus viewed from a further aspect the invention provides a process for the preparation of macrocyclic tetrazacycloalkanes, said process comprising (i) reacting a diamine with a bridging agent to couple four amine nitrogens to a bridging moiety to yield a fused bicyclic intermediate, (ii) reacting said intermediate to introduce alkylene bridges between the coupled amine nitrogens to yield a fused tetracyclic intermediate, and (iii) decoupling said bridging moiety to yield a macrocyclic tetraazacycloalkane.

Following production of the macrocyclic tetraazacycloalkanes according to the process of the invention, and if necessary the reduction of any ring carbonyl groups, the products will generally be subjected to N-alkylation in order to produce the desired chelating agents. The N-alkylation step to introduce desired alkyl or substituted alkyl groups onto the macrocyclic skeleton can be performed using conventional alkylation techniques, for example involving reaction with an alkylhalide $R^2$-Hal (where Hal is a halogen atom such as chlorine or bromine and $R^2$ is an alkyl group optionally substituted, for example by hydroxy or alkoxy groups or by chelant moieties, such as carboxyamide groups or carboxyl or phosphonic acid groups (optionally protected by ester groups)). The alkyl moiety in $R^2$ will conveniently contain 1 to 6 carbon atoms and any chelant moiety will preferably be on the alpha or beta carbon. If a protected chelant group is introduced in this fashion, it may subsequently be deprotected, for example by ester cleavage to make the group available for metallation.

Metallation of the macrocyclic chelating agent may be effected by conventional methods, for example as described in the patent literature relating to MR contrast agents (see for example EP-A-71564, EP-A-130934, EP-A-165728, EP-A-258616, WO-A-86/06605, etc.).

The choice of metal ions to be complexed will depend upon the intended end use for the chelate complex. Especially preferred are ions of metals of atomic numbers 22 to 32, 42 to 44, 49 and 57 to 83, in particular Gd.

Where the chelate is to be used as an MR contrast agent, the chelated metal species is conveniently a paramagnetic ion of a transition metal or a lanthanide, preferably having an atomic number of 21 to 29, 42, 44 or 57 to 71. Complexes of Eu, Gd, Dy, Ho, Cr, Mn and Fe are especially preferred and $Gd^{3+}$, $Mn^{2+}$ and $Dy^{3+}$ are particularly preferred ions. For use as contrast agents in MRI, the paramagnetic metal species is conveniently non-radioactive as radioactivity is a characteristic which is neither required nor desirable.

Where the chelate complex is to be used as an X-ray or ultrasound contrast agent, the metal is preferably a heavy metal such as a non-radioactive metal with an atomic number greater than 37, preferably greater than 50, for example $Dy^{3+}$.

Where the metal complex is to be used in scintigraphy or radiotherapy, the chelated metal species must of course be radioactive and any conventional complexable radioactive isotope, such as $^{99m}Tc$ or $^{111}In$ for example may be used. For radiotherapy the chelated metal may for example be $^{153}Sm$, $^{67}Cu$ or $^{90}Y$.

In the definitions of the reagents given above, unless otherwise stated, alkyl groups preferably contain 1 to 6 carbon atoms, especially 1,2,3 or 4 carbons and optionally substituted alkyl groups may carry substituents selected from aryl (in particular phenyl and substituted phenyl), hydroxy, oxo, amino, and alkoxy groups or chelant or substituted chelant moieties such as are described for $R^2$.

All particulars referred to herein are hereby incorporated herein by reference.

The invention is illustrated further by reference to the following non-limiting Examples:

EXAMPLE 1

Condensation of glyoxal with triethylenetetramine: To a flask was added 10 g (61 mmol) of triethylenetetramine mono-hydrate and 200 mL of absolute ethanol. To this solution was added 8.9 g (61 mmol) of 40% aqueous glyoxal. After stirring overnight at ambient temperature the solvent was evaporated to afford the 5,6,5-tricyclic product 1 as an amber oil (75–80% purity). This material was used directly in the subsequent step.

EXAMPLE 2

Condensation of dibromoethane with 1: Crude 1 was dissolved in ten parts (by volume) of dimethylformamide. To this solution was added 1.5 mole equivalent of dibromoethane. The solution was stirred for 20 hours at ambient temperature. After removing the solvent and excess dibromoethane under reduced pressure the product 2 was isolated by flash chromatography (silca gel/$CH_3CN$:$NH_3$:EtOH). The yield of 2 is ca. 70% based on 1.

EXAMPLE 3

1,4,7,10-tetraazacylododecane 3 (cyclen): 2 was added to ca. 20 parts by volume of absolute ethanol and 10 mole equivalents of hydroxyamine. The suspension was heated to reflux for 16 hours. Slow cooling gave 3 as an off-white precipitate which was collected by filtration and washed with cold ethanol. The yield of 3 was 80% based on 2.

EXAMPLE 4

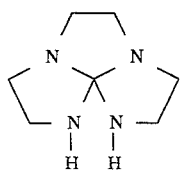
4

Triethylenetetraamine is reacted with ethyl orthocarbonate (C(OEt)$_4$) in absolute ethanol. The 5,5,5 tricyclic intermediate 4 formed is divided into batches and used in subsequent Examples.

EXAMPLE 5

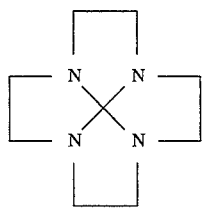
5

5,5,5-tricyclic intermediate 4 is reacted with 1,2-dibromoethane in DMF under a nitrogen atmosphere to yield the 5,5,5,5 fused tetracyclic intermediate 5 which is treated with aqueous acid to yield cyclen 3.

EXAMPLE 6

5,5,5-tricyclic intermediate 4 is treated with HCl and subsequently sequentially with ClCH$_2$CHO and NaBHCN to yield cyclen 3.

EXAMPLE 7

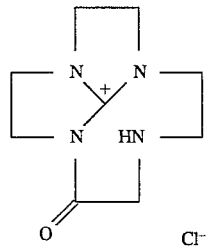
6

5,5,5-tricylic intermediate 4 is treated with HCl and subsequently with ClCH$_2$COCl. The 5,5,8 tricyclic intermediate 6 which is formed is then reduced with lithium aluminium hydride to yield cyclen 3.

EXAMPLE 8

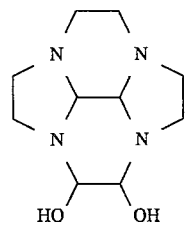
7

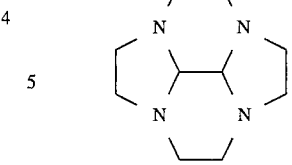
8

One equivalent of triethylenetetraamine is reacted with two equivalents of glyoxal in water. The C$_2$ bridged 5,6,5,6 tetracyclic intermediate 7 formed is reduced with NaBHCN to yield a 5,6,5,6 tetracyclic product 8 which is then reacted with hydroxylamine to strip out the central C$_2$ bridge.

EXAMPLE 9

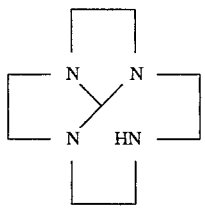
9

5,5,5-tricyclic intermediate 4 is reacted with 1,2-dibromoethane and subsequently reduced with NaBHCN to yield a 5,5,8 tricyclic intermediate 9.

EXAMPLE 10

Under a nitrogen atmosphere the 5,5,8 tricyclic intermediate 9 is N-benzylated with benzyl chloride and then treated with sulphuric acid to yield mono-N-benzylcyclen 10. The N-benzyl group may function as a temporary protecting group to be removed after substitution of the remaining ring nitrogens to yield DO3A or DO3A analogues. However in place of N-benzylation other N-alkylations may be performed analogously, e.g. to introduce hydroxyalkyl groups.

EXAMPLE 11

N-benzylcyclen 10 is reacted with bromoacetic acid in sodium hydroxide solution pH 10 to yield N-Benzyl-DO3A 11. If desired t-butyl bromoacetate or benzyl bromoacetate may be used in place of bromoacetic acid.

We claim:

1. A process for the preparation of macrocyclic tetraazacycloalkanes, said process comprising (i) reacting a tetraazaalkane with a bridging agent to couple four amine nitrogens of said tetraazaalkane to a bridging moiety to yield a fused tricyclic intermediate, (ii) reacting said intermediate to introduce an alkylene bridge between the secondary amine nitrogens in the outer rings of the fused tricyclic intermediate, optionally by decoupling an alkanediylidene bridging moiety from the tertiary amine nitrogens at the ring fusion sites of the fused tricyclic intermediate, and (iii) where necessary, decoupling said bridging moiety to yield a macrocyclic tetraazacycloalkane.

2. A process as claimed in claim 1, being a process for the preparation of macrocyclic tetraazacyclododecanes of formula I

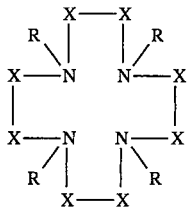

(I)

where each R independently is hydrogen or optionally substituted alkyl and each X independently is $CH_2$, CHR or a carbonyl group.

3. A process as claimed in claim 1 wherein step (i) is effected to yield as said tricyclic intermediate a compound of formula

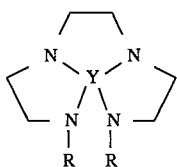

where Y is a carbon atom or a metal ion, R is as defined in claim 2 and the backbone carbons are optionally substituted by R groups.

4. A process as claimed in claim 1 wherein step (i) is effected to yield as said tricyclic intermediate a compound of formula

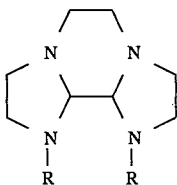

where R is as defined in claim 2 and the backbone carbons are optionally substituted by R groups.

5. A process as claimed in claim 4 wherein step (i) involves reacting a triethylenetetraamine with glyoxal whereby to yield said tricyclic intermediate.

6. A process as claimed in claim 4 wherein said tricyclic intermediate is converted to said macrocyclic tetraazacycloalkane by reaction with a difunctional bridging agent serving to introduce a $C_2$ bridging moiety and by subsequent decoupling of the $C_2$ bridging moiety.

7. A process as claimed in claim 6 wherein said difunctional bridging agent is a haloacetylhalide, an alkyl halide epoxide or a compound of formula LvCHRCHRLv where L is a displaceable leaving group and R is as defined in claim 2.

8. A process as claimed in claim 6 wherein decoupling of the $C_2$ bridging moiety is effected by reaction with hydroxylamine or acid.

9. A process as claimed in claim 4 wherein said tricyclic intermediate is converted to said macrocyclic tetraazacycloalkane by reaction with glyoxal to introduce a $C_2$ bridging moiety and by subsequent reduction and decoupling of the $C_2$ bridging moiety.

10. A process as claimed in claim 9 wherein macrocyclic tetraazacycloalkane preparation is effected by reaction of a triethylenetetraamine with glyoxal, reduction and decoupling in a one-pot reaction.

11. A process as claimed in claim 4 wherein conversion of the tricyclic intermediate to the macrocyclic tetraazacycloalkane is effected by metallation to partially decouple the central bridging moiety in the tricyclic intermediate, followed by demetallation to yield the macrocyclic tetraazacycloalkane.

12. A process as claimed in claim 3 wherein said tricyclic intermediate is prepared by reaction of a triethylenetetraamine with an alkylorthocarbonate.

13. A process as claimed in claim 3 wherein conversion of a said tricyclic intermediate wherein Y is a carbon atom to said macrocyclic tetraazacycloalkane is effected by reaction of the tricyclic intermediate with a bifunctional bridging agent and by subsequently decoupling the $C_1$ bridging moiety residue of Y.

14. A process as claimed in claim 3 comprising cyclising a tricyclic intermediate in which Y is carbon and one N-attached R group is a protected carboxy group.

15. A process as claimed in claim 3 wherein said tricyclic intermediate is converted to a 5,5,8 intermediate of formula

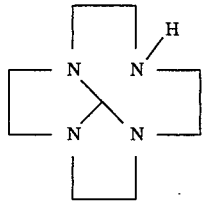

(wherein the backbone carbons are optionally substituted by R groups) which is N-monoalkylated by reaction with an alkylating agent before decoupling of the $C_1$ bridging moiety residue of Y.

16. A process as claimed in claim 15 wherein the N-monoalkylated macrocyclic tetraazacycloalkane produced by said decoupling is N-alkylated by reaction with a further alkylating agent whereby to produce a compound of formula

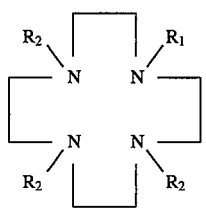

(wherein $R_1$ and $R_2$ are optionally substituted alkyl groups, $R_2$ being different from $R_1$ and wherein the backbone carbons of the macrocyclic ring are optionally substituted by R groups), optionally followed by removal of the $R_1$ group and N-alkylation by reaction with a third alkylating serving to introduce an N-attached $R_3$ group (where $R_3$ is an optionally substituted alkyl group and $R_3$ and $R_2$ are different).

17. A process as claimed in claim 3 wherein a tricyclic intermediate in which Y is a metal ion is converted to a macrocyclic tetraazacycloalkane by reaction with a bifunctional bridging agent, followed by demetallation.

18. A process as claimed in claim 3 wherein a tricyclic intermediate in which Y is a metal ion is converted to a macrocyclic tetraazacycloalkane by reaction with formaldehyde and hydrogen sulphide, followed by desulphurization and demetallation.

19. A process for the preparation of macrocyclic tetrazacycloalkanes, said process comprising (i) reacting a diamine with a bridging agent to couple four amine nitrogens to a bridging moiety to yield a fused bicyclic intermediate, (ii) reacting said intermediate to introduce alkylene bridges between the coupled amine nitrogens to yield a fused tetracyclic intermediate, and (iii) decoupling said bridging moiety to yield a macrocyclic tetraazacycloalkane.

20. A process as claimed in claim 1 wherein following conversion of said tricyclic intermediate to a macrocyclic tetraazaalkane, said macrocyclic tetraazaalkane is N-alkylated by reaction with an alkylating agent.

21. A process as claimed in claim 20 wherein said alkylating agent is of formula $R^2$-Hal (where Hal is a halogen atom and $R^2$ is an alkyl group optionally substituted by hydroxy or alkoxy groups or by chelant moieties optionally protected by ester groups).

22. A process as claimed in claim 20 wherein the N-alkylated macrocyclic tetraazacycloalkane is subsequently metallated.

23. A process as claimed in claim 22 wherein metallation is with paramagnetic transition metal or lanthanide metal ions.

24. A process as claimed in claim 19 wherein following conversion of said tetracyclic intermediate to a macrocyclic tetraazaalkane, said macrocyclic tetraazaalkane is N-alkylated by reaction with an alkylating agent.

25. A process as claimed in claim 24 wherein said alkylating agent is of formula $R^2$-Hal (where Hal is a halogen atom and $R^2$ is an alkyl group optionally substituted by hydroxy or alkoxy groups or by chelant moieties optionally protected by ester groups).

26. A process as claimed in claim 24 wherein the N-alkylated macrocyclic tetraazacycloalkane is subsequently metallated.

27. A process as claimed in claim 26 wherein metallation is with paramagnetic transition metal or lanthanide metal ions.

* * * * *